United States Patent [19]

Brunnschweiler et al.

[11] Patent Number: 5,047,640
[45] Date of Patent: Sep. 10, 1991

[54] WEB INSPECTING METHOD

[76] Inventors: David Brunnschweiler, Balderstone Lodge, Commons Lane, Balderstone, Blackburn, Lancs.; Neil R. Henderson, 2 Southcliffe, Great Harwood, Lancashire, BB2 7PP, both of England, BB6 7PP; David W. Swift, 8 Bryntiron Avenue, Prestatyn, Clwyd, LL19 9PB, Wales

[21] Appl. No.: 467,177

[22] Filed: Jan. 19, 1990

[30] Foreign Application Priority Data

Jan. 19, 1989 [GB] United Kingdom ............... 8901192
Jan. 28, 1989 [GB] United Kingdom ............... 8901921

[51] Int. Cl.⁵ ............................................. G01N 21/89
[52] U.S. Cl. ..................................... 250/341; 250/563; 250/572; 356/431
[58] Field of Search ...................... 250/341, 572, 563; 356/431

[56] References Cited

U.S. PATENT DOCUMENTS

| 4,103,177 | 7/1978 | Sanford et al. | 250/562 |
| 4,224,513 | 9/1980 | Casey et al. | 250/216 |
| 4,402,609 | 9/1983 | Fetzer et al. | 356/387 |
| 4,631,408 | 12/1986 | Zelmanovic et al. | 250/339 |
| 4,715,717 | 12/1987 | Evans | 356/429 |
| 4,733,080 | 3/1988 | Brunnschweiler et al. | 250/341 |
| 4,879,471 | 11/1989 | Dahlquist | 250/359.1 |
| 4,937,449 | 6/1990 | Kreuzer et al. | 250/351 |

FOREIGN PATENT DOCUMENTS

| 0037669 | 10/1981 | European Pat. Off. . |
| 0069061 | 1/1983 | European Pat. Off. . |
| 0182471 | 5/1986 | European Pat. Off. . |
| 0258150 | 3/1988 | European Pat. Off. . |
| 2009001 | 9/1971 | Fed. Rep. of Germany . |
| 52-29789 | 3/1977 | Japan .................................. 356/431 |

*Primary Examiner*—Constantine Hannaher
*Attorney, Agent, or Firm*—Charles J. Brown

[57] ABSTRACT

A web e.g. a fibre web as used in the manufacture of textiles is inspected e.g. for thickness uniformity or the like by transillumination, where the web is subject to ambient illumination, the transillumination being effected in modulated fashion whereby to distinguish measuring illumination from ambient illumination. Modulation may be effected by time-chopping a beam or by a narrow spectral band filter to improve signal-to-noise ratio.

6 Claims, 3 Drawing Sheets

WEB INSPECTING METHOD

This invention relates to methods and apparatus for monitoring webs of material and particularly travelling webs such as paper and textile webs.

Webs are monitored for a variety of reasons, including colour, reflectance, transmittance and so on, which might inter alia indicate uniformity of dye application or thickness or homogenity of web structure.

Among problems experienced in this field of endeavour figure ambient light, which may be variable, and affect readings on a temporal or spatial basis as the intensity of ambient light changes over time or by for example shadows falling across the web;

non-uniformity of the distribution of light over the web-e.g. in some prior art proposals, fluorscent tubes have been used presupposing a uniform distribution of light emission end-to-end, now found to be inadequately uniform for many applications;

changes in light emission from the light source over time, with fluctuating voltage supply or ageing of the source.

The present invention provides means for solving the first of these problems and further inventive features deal also with the other problems.

This invention comprises a method for inspecting a web of material by transillumination, where the web is subject to ambient illumination, comprising illuminating the web in modulated fashion whereby to distinguish measuring illumination from ambient illumination.

The method may be adapted for monitoring web density by measuring the reduction in light intensity of light passed through the web. The light may be passed twice through the web before the measurement—this, provided the light passes twice through the same place on the web, may enhance the sensitivity of the measurement.

Light from a source, which may be point-like or extended, may be traversed over the web, as by reflection from a moving mirror. Such a mirror may be rotated or oscillated so as to traverse the light from edge to edge of a travelling web and may be so rotated or oscillated, for example, by a stepper motor or by a d.c. motor whose position is monitored e.g. by a shaft encoder.

Light passing through the web may be reflected back towards the source by a reflector behind the web. Such reflector may be a retroreflecting screen such as may be made by reflecting paint incorporating ballotini.

Light from the source may be measured by a single detector.

Variability of the intensity of the modulated illumination may be compensated for by detecting illumination therefrom unaffected by the web. Light passing through the web may be reflected back through the web by reflector means behind the web, the reflector means extending beyond the web so as to reflect to a detector modulated illumination which has not passed through the web.

The modulated illumination may be with visible light or infra red light and may be by a laser, when modulation may be effected by switching the laser on and off or by using a pulsed laser or by varying a laser output, as by using a modulator element such as a beam chopper or by using a narrow spectral band filter to improve signal-to-noise ratio, this latter filter technique implying perhaps a wider definition of modulation than is customary.

The invention also comprises apparatus for inspecting a web of material by transillumination, where the web is subject to ambient illumination, comprising modulated illumination means for transilluminating the web and detector means adapted to detect illumination from the web and distinguish the modulated illumination from ambient illumination.

The method may be carried out by apparatus which may comprise laser means as said modulated illumination means directing a beam of light at a rotating or oscillating mirror through a beam-splitter, the mirror directing the beam to traverse across the width of a travelling web behind which is a reflector directing the beam passing through the web and redirecting it back towards the mirror whence to the beamsplitter which directs the thus reflected light to a detector, the detector being adapted (as by being synchronised) with respect to the laser means so as to be able to distinguish the modulated illumination from the ambient illumination.

Embodiments of apparatus and methods for inspecting a web of material according to the invention will now be described with reference to the accompanying drawings, in which.

Figure 1:
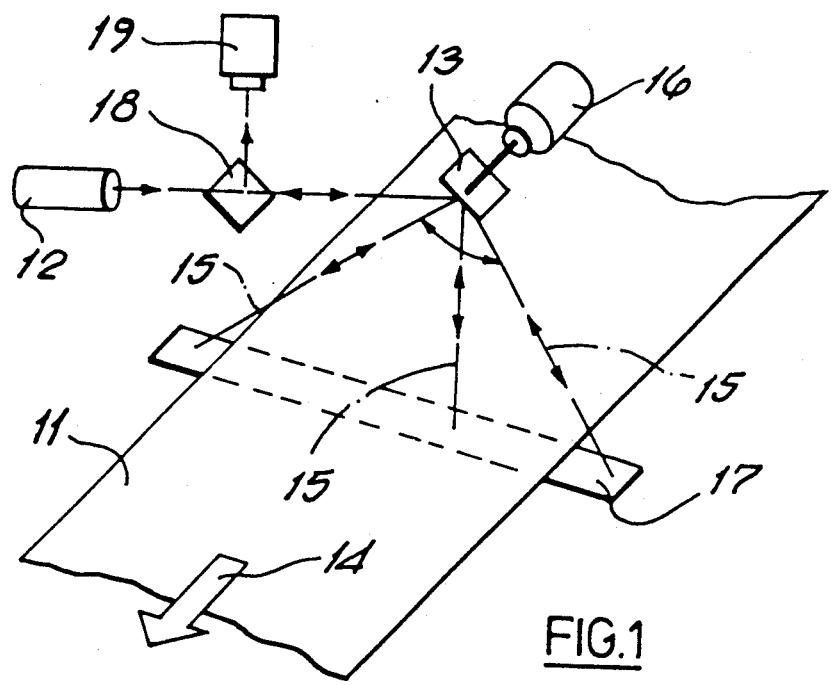
FIG. 1 is a diagrammatic perspective view of a web monitoring arrangement.

The drawings illustrate a method and apparatus for inspecting a web 11 of material by transillumination, where the web 11 is subject to ambient illumination.

Such inspection might be required, for example, in textile or paper making operations. In a textile fibre preparation plant, a card web intended for making yarn or a cross-folded card web intended for making non-wovens may be required to be monitored for regularity of area density. Such webs can be so monitored by transillumination, information about the area density being derived from the extent to which light shone through the web is attenuated. It is found that visible light is a good indicator of the area density of thin webs while for thicker webs in which most, say 80% at least, of the light is blocked by fibres, infra red radiation which passes through the fibres can give a similarly good area density indication.

Ambient illumination, however, interferes with such measurements, and it is difficult to exclude it totally by shielding.

In accordance with the invention, the web 11 is illuminated in modulated fashion by a light source 12 whereby to distinguish measuring illumination, from the source 12, from ambient illumination.

The method is adapted for monitoring web density of a travelling web 11, by measuring the reduction in light intensity of light passed through the web 11. As illustrated, the measuring light is passed twice through the web 11 before the measurement. Whilst this is, in the illustrated arrangement, highly convenient, it also results in increased sensitivity.

The light source 12 is a conveniently point-like source, though an external source could also be used, and light from it is traversed over the web 11 by reflection from a moving mirror 13. The direction of web travel is indicated by the arrow 14—the light beam 15 is traversed from edge to edge of the web 11 by the mirror 13 oscillating about an axis parallel to the arrow 14. The mirror, which could then be multi-faceted, could equally well rotate and in fact this may be a simpler mechanical arrangement.

The mirror 13 is a lightweight but rigid mirror mounted on the shaft of a stepper motor 16. Such a motor desirably has 26,000 steps per revolution, more desirably twice that number, and is capable of some 7,000 revolutions per minute. The motor 16 is controlled so as to oscillate the mirror 13 over an angle such as oscillates the beam 15 right across the travelling web 11 and to some small extent either side thereof. Whilst a stepper motor is convenient from a control point of view, if high traverse speeds are required a d.c. motor or galvanometer-type drive, perhaps with a shaft encoder for position determination, could be substituted.

The beam 15 is reflected back towards the point-like source 12 by a reflector 17 behind the web 11. The reflector 17 is a retroreflecting screen utilising microbeads so that incident light is reflected back in the direction whence it came. Thus light from the oscillating mirror 13 is reflected straight back thereto no matter at what angle it strikes the screen 17. Light striking the oscillating mirror 13 from the screen 17 is reflected back towards the source 11, the oscillating mirror not having moved perceptibly in the short time it takes for the light to leave it and return to it. In fact, it may be desirable in many instances if the motor 16 moves the mirror 13 stepwise so that the beam dwells a short period of time for a measurement to be made.

A beamsplitter 18 is situated in the path between the source 12 and the mirror 13. This allows light from the source 12 to reach the mirror 13 and directs light returned from the mirror 13 to a silicon photodiode detector 19. A polarising beamsplitter and a quarter wave plate can be used to improve the amount of light reflected to the detector.

The light source 12 is a helium-neon laser, which gives a narrow coherent beam. A laser of 0.5 mW power will be adaequate for most fibre webs; higher powered lasers, e.g. 1.5 mW, will be more suitable for heavier textiles. Infra red lasers can be used instead of visible light lasers for dense webs where transmission is then predominantly through rather than between fibres.

Some lasers are pulsed lasers, i.e. inherently delivering light intermittently. Such are of course inherently modulated. Where a continuous laser is used, it can be modulated by switching it on and off or by varying its intensity in some way, or by a beam chopper. The rate of pulsing in whatever fashion should be such as, where individual measurements are being made at "dwell" points in the traverse across the web, pulsing or modulation must be apparent during such measuremnts. This, of course, means that switching the laser on and off may best be effected electronically.

Figure 5:
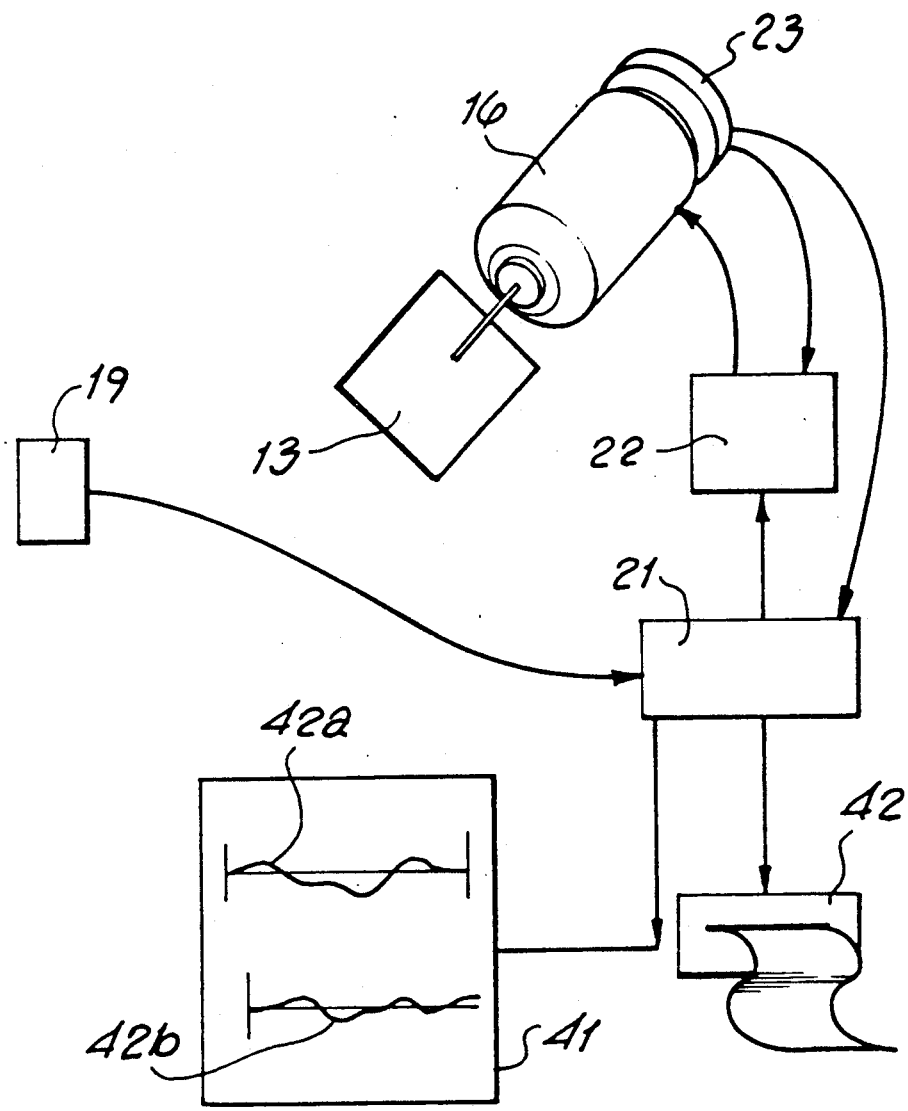
FIG. 5 is a schematic showing the control arrangement of the monitoring arrangement.

After attenuation by its passage through the web 11, the modulated beam 15 is sensed by the photodiode 19 and an electrical output therefrom is analysed by a microprocessor or computer 21, FIG. 5. For a regular mark/space modulation, the electrical signal will contain a set of low "space" levels corresponding to ambient illumination alone. It is a simple matter for the computer to separate the two levels and average each of them, subtract the low level average from the high level average and output the result in numerical form. Such should then be independent of the level of ambient illumination.

More sophisticated modulation may be employed where ambient illumination may itself contain oscillatory components, as for example from fluorescent lighting. Here a pattern of on/off periods can be imposed on the source 11 and electronically synchronised in the microprocessor or computer 21—the latter, in fact, may generate signals controlling the light source 11.

The microprocessor or computer 21 may also provide the driving pulses for the stepper motor 16, so that the latter can readily be adjusted as to traverse width, speed and frequency by keyboard input and system software, there being if required a motor drive encoder 22 for such purpose (FIG. 5).

The microprocessor or computer 21 may well then "know" where on the web the mirror 13 is directing the beam 15, or this information may be derived from or verified by a motor shaft encoder 23.

The beam location information is then combined with the photodiode information to give an obscuration distribution across the web 11 and such can be represented graphically on a VDU 41 (FIG. 5) as in top trace 42a which is essentially an area density distribution transversely of the web 11.

Coupling this information with web travel speed information derived e.g. from a component of the web producing or processing machinery allows a second graphical representation to be made on the VDU this time of area density distribution lengthwise of the web-trace 42.

All of this information can, of course, be differently displayed if desired, for example, numerically, and may be output in hard copy on a printer 42.

The light source 11 may be variable in intensity or other factors may change with time such for example as the response of the photodiode 19 or the performance of other optical components of the system. It is arranged, to compensate for such variability, that the system is calibrated from time to time, and this can for greatest assurance of accuracy be done before and after each traverse of the beam 15. As noted above, the screen 17 extends beyond either side of the web 11 so that the beam 15 can "see" the screen 17 without the intervention of the web 11. An intensity measurement at these extreme traverse positions sets the base level of illumination for the traverse against which the observation caused by the web can be evaluated. The calibration could, of course, be carried out on light captured more directly from the source without having to provide the extension of the screen 17 beyond the web—the latter, however, has the advantage that the light has travelled more or less the same distance through the same atmosphere for both actual and calibration intensity measurements.

Figure 2:
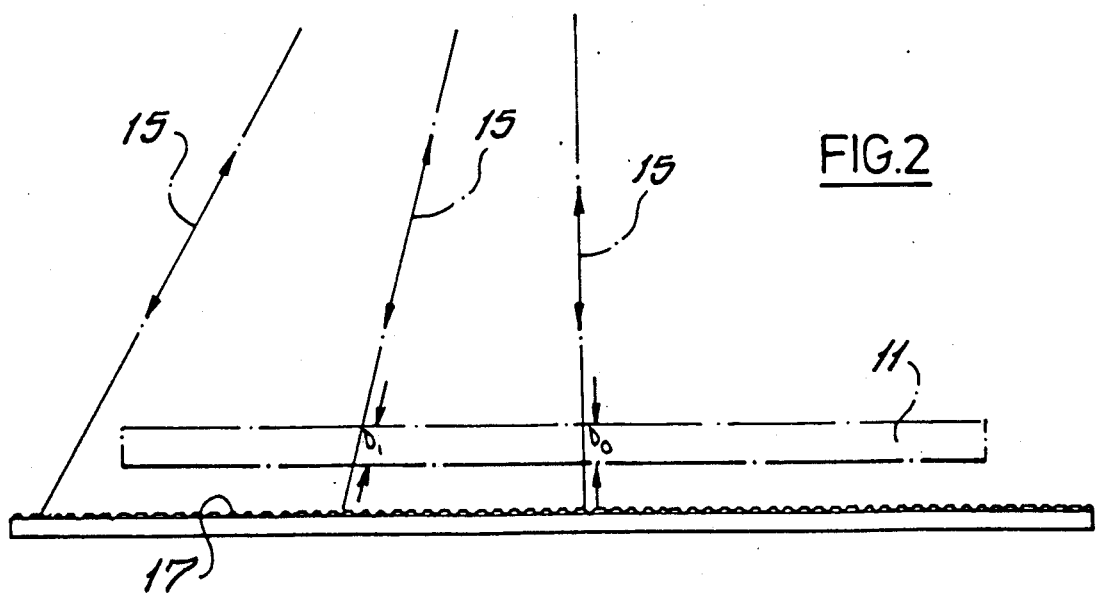
FIG. 2 is a transverse section of the web region of FIG. 1.

A problem to be dealt with in the illustrated arrangement is best seen in FIG. 2 where three beam 15 positions are shown. The left-hand beam 15 is the calibrating beam at extreme traverse. The right-hand beam is at the mid-line of the web directly beneath the oscillating mirror 13. The middle beam is seen to be angled with respect to the right-hand beam and the path length $D_1$ through the web 11 is greater than the corresponding length $D_0$ of the right-hand beam. The relationship would appear to be a simple trigonometrical one, but this must be approached with caution as the nature of the web might complicate matters-because of fibre orientation, light might penetrate preferentially at some angles. So experience with different types of web might suggest that calibration in this regard also be effected.

The calibration may take the form of preliminary measurements on particular web types which give rise to a correction function which can be applied to the photodiode output dependent on the instantaneous beam angle or position.

Figure 6:
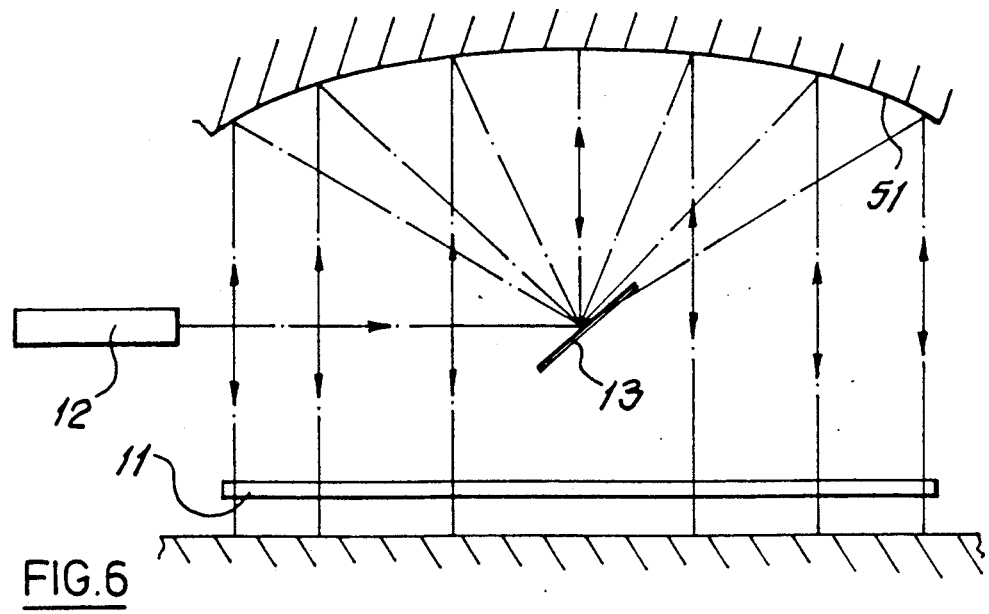
FIG. 6 is a diagrammatic section through another arrangement.

The problem posed by the angular dependence of the beam path length through the web 11 can of course be avoided by ensuring that the beam always passes through at the same angle, preferably perpendicularly. This can be done by an arrangement as illustrated in FIG. 6 where the beam 15 from the light source 11 is deflected by the mirror 13 upwardly to a parabolic mirror 51 whence it is reflected vertically downwardly no matter what the position of the mirror 13. The reflector 17 behind the web 11 can then be a simple specular reflector. Such an arrangement might be cumbersome in practice. However, the parabolic mirror 51 might be replaced by a Fresnel mirror which will not occupy the same vertical extent as a truly parabolic mirror, or a Fresnel lens could be interposed between the mirror 13 and the web 11, to refract the beam so as to pass perpendicularly through the web 11.

These arrangements would appear cumbersome in practice by comparison with the retro-reflecting screen arrangement principally described.

Figure 3:
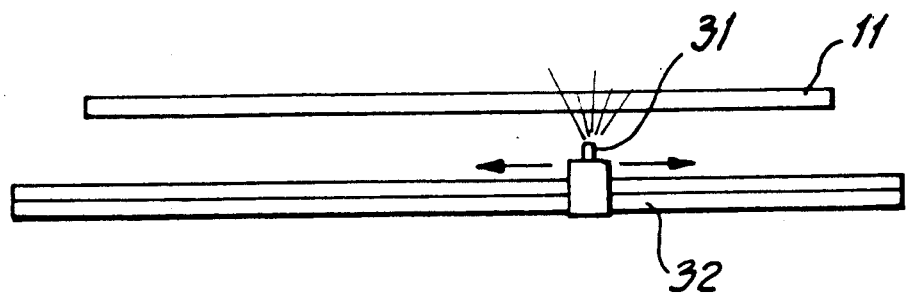
FIG. 3 is a diagrammatic plan view of a mirror of FIG. 1 with a fly clearing arrangement therefor.

FIG. 3 illustrates a clearing arrangement for the screen 17 in which an air-blowing nozzle 31 is traversed from end to end thereof by a rodless air cylinder 32. In a fibre plant, fibre and fly will tend to drop from the web 11 which would, were it not cleaned away regularly, impair the performance of the system, particularly if the accumulation were different at the extreme mirror positions so that the traverse-on-traverse calibration procedure became unreliable.

Figure 4:
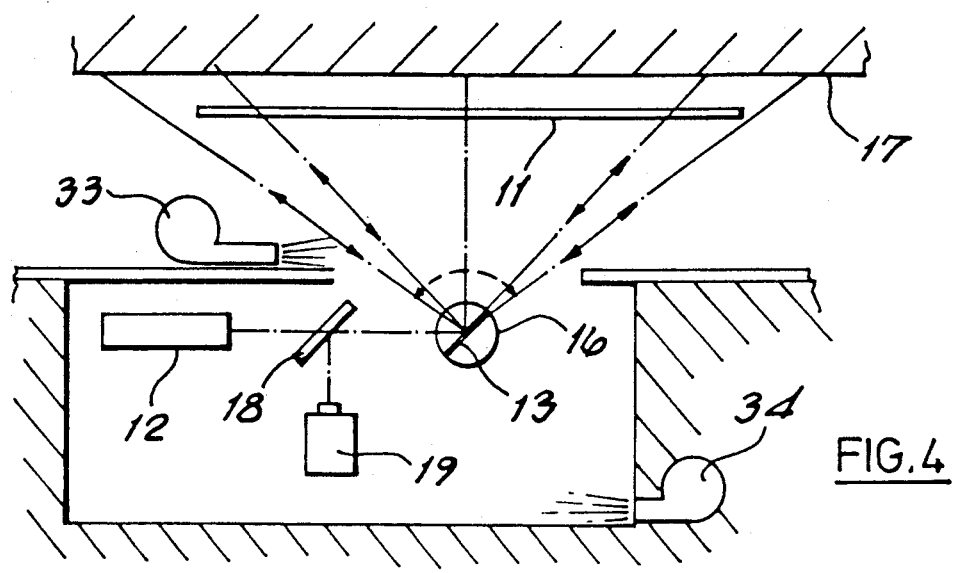
FIG. 4 is a cross-section showing another configuration with fly clearing.

FIG. 4 illustrates another configuration in which the screen 17 is above the web 11 and therefore in a position in which fly will not tend to accumulate on it. The laser 12, mirror 13 and associated equipment is beneath the web 11, if necessary in a pit, if there is insufficient space between web and floor to accommodate it. A simple blower 33 can keep fly away from this equipment, or the pit may be held at a slight over-pressure as by a fan 34 so that the net airflow through its aperture is outwards.

With a 7,000 rpm stepper motor and a traverse angle of 120°, which means the mirror 13 turns through an angle of 60° for each beam traverse, traverse frequencies of some hundreds of traverses per second can be contemplated. With a one meter web width a traverse angle of 60° (30° of the mirror 13), and a 26,000 step-per-revolution motor 16, there can be up to about 850 separate dwell points between steps made. In practice it is probable that one measurement per centimeter would be quite sufficient for most purposes, but clearly with a 52,000 step motor, resolution can easily be brought down to millimeter levels.

If a web is traversed in say 0.01 seconds and, say 100 measurements made, each measurement must take place in somewhat less than 0.1 milliseconds. The modulation rate must be faster than this, of course, and the light source must pulse, therefore, at a rate in the order of $10^5$ Hz at least.

It is not necessary to use a laser as the light source 12, of course. A strobing discharge lamp with suitable optics could be used, and also a quartz-halogen filament lamp with mechanical strobing as by a beam chopper which could, also, of course, be used with a laser. But a laser clearly has advantages in terms of beam fineness and intensity.

For a web travelling at one meter per second, traversing the beam every 0.01 second results in measurements being made at centimeter intervals along the web.

Instead of modulating the measuring illumination by varying its intensity with time, modulation could also be effected in the sense of using illumination with a special spectral signature, which may be produced by a narrow spectral bandwidth filter. Applying such a filter to the detector so as to match the characteristics of the source (whether those characteristics are inherent or produced by a like filter) will improved the signal-to-noise ratio facilitating detection even in ambient light conditions which would otherwise interfere.

We claim:

1. A method of inspecting travelling web material subject to ambient light which comprises
   a) emitting light from a light source,
   b) modulating the emitted light into alternating on and off pulses,
   c) traversing the modulated light back and forth from edge to edge across the web transverse to its direction of travel, so that it travels along a first path which passes through the web to emerge therefrom with a reduced intensity,
   d) measuring the intensity of the sum of the emitted light beam passing through the web plus ambient light during the on pulses and measuring the intensity of ambient light alone during the off pulses to yield a measurement of the intensity of the emitted light alone passing through the web during the on pulses independent of ambient light, and
   e) measuring the intensity and variations thereof of the emitted light travelling along a second path the same length and through the same atmosphere as the first path, but not passing through the web during some of the on pulses and comparing the same to said yielded measurements of the intensity and variations thereof of the emitted light alone passing through the web during the on pulses in order to monitor web properties irrespective of variations in intensity of light emitted from the light source.

2. A method according to claim 1 wherein the modulated light after its passage through the web is reflected back to pass again through the web a second time before the intensity measurements are made.

3. A method according to claim 2 wherein the reflection of the modulated light after its first passage through the web is accomplished by a retro-reflecting mirror.

4. A method according to claim 2 wherein the comparative intensity measurements are made by a single detector.

5. A method according to claim 1 wherein the modulated light is traversed across the web by reflection from a moving mirror.

6. A method according to claim 1 wherein the light source is a laser and the modulation is effected by one of switching the laser on and off and by pulsing.

* * * * *